United States Patent

Bombe

[11] Patent Number: 6,141,940
[45] Date of Patent: Nov. 7, 2000

[54] DEVICE FOR CONTINUOUS CONTROLLING OF THE CONTENTS OF HERMETICALLY SEALED CONTAINERS

[75] Inventor: Didier Bombe, Dury, France

[73] Assignee: AES Laboratoire, Societe Anonyme Ayant Son Siege Social, Combourg, France

[21] Appl. No.: 09/011,394
[22] PCT Filed: Jun. 2, 1997
[86] PCT No.: PCT/FR97/00957
§ 371 Date: Jan. 14, 1999
§ 102(e) Date: Jan. 14, 1999
[87] PCT Pub. No.: WO97/46875
PCT Pub. Date: Dec. 11, 1997

[30] Foreign Application Priority Data

Jun. 5, 1996 [FR] France .................. 96 06922

[51] Int. Cl.[7] .................................. B65B 31/02
[52] U.S. Cl. .................... 53/432; 53/510; 53/167; 73/863.81; 73/863.85
[58] Field of Search .................. 53/167, 432, 510, 53/53; 73/863.81, 863.85, 864.74

[56] References Cited

U.S. PATENT DOCUMENTS

| | | |
|---|---|---|
| 3,186,232 | 6/1965 | Yates et al. . |
| 3,849,070 | 11/1974 | Garza et al. . |
| 3,960,670 | 6/1976 | Pflug . |
| 4,096,734 | 6/1978 | Khayat . |
| 4,133,736 | 1/1979 | Nakagawa et al. . |
| 5,822,951 | 10/1998 | Rosik ................................... 53/432 |

FOREIGN PATENT DOCUMENTS

| | | | |
|---|---|---|---|
| 0 567 782 A1 | 11/1993 | European Pat. Off. | ......... G01N 1/00 |
| 2 109 274 | 5/1972 | France | ............... G01I 21/00 |
| 2 711 803 | 5/1995 | France | ............... G01N 33/02 |
| 3439778 A1 | 4/1986 | Germany | ............ G01N 1/24 |

Primary Examiner—Linda Johnson
Attorney, Agent, or Firm—Michael R. Schacht; Hughes & Schacht, P.S.

[57] ABSTRACT

The device is characterised in that the obturating means are constituted by an obturating screw (24) capable of co-operating with the whole set of mounting pieces (3) and, if required, with a ring-shaped obturating joint (25) and in that the capturing means are constituted by a threaded joining piece (25) to co-operate with the whole set of mounting pieces (3) by replacing the obturating screw (24) and, if required, the ring-shaped obturating joint (25) during the control, so as to break the imperviousness of the receiving cell (6) with respect to the container or box and comprising a perforation (34) linked to continuous analysing means so as to enable capture of the gas that has entered the receiving cell (6).

27 Claims, 4 Drawing Sheets

DEVICE FOR CONTINUOUS CONTROLLING OF THE CONTENTS OF HERMETICALLY SEALED CONTAINERS

RELATED APPLICATIONS

This application claims priority of PCT/FR97/00957 filed Jun. 2, 1997, which claims priority of French Application Ser. No. 96/06922 filed Jun. 5, 1996.

The present invention relates to a device permitting continuous control of the contents of containers comprising a can body hermetically sealed by a lid crimped onto it.

The device can advantageously be used to control the stability of preserve cans belonging to one batch and prepared at the same time as one another in the same process, and, generally, to check the stability of products subjected to a thermal treatment conferring on them biological stability at ambient intermediate-storage temperature.

In order to guarantee consumer safety, the Authorities require that preserves be subjected to very strict controls, in particular defined by the AFNOR standards NFV 08 401 and NFV 08 402.

Those controls, which aim to check the consumable nature of preserves, basically involve placing several cans or jars from the same batch in an oven at a temperature favouring the development of micro-organisms, and then analysing their contents, after opening them, at the end of a specific incubation period.

Those analyses, which are especially measurements of differences in pH, are carried out in each case on a series of at least three cans, namely a control can, a can which has been incubated for seven days at 55° C. and a can which has been incubated for seven days at 37° C. or for twenty-one days at 32° C.

When the measured difference in pH is less than 0.5 and if no change in appearance or texture is detected, the preserve is considered to be stable and perfectly consumable; if this is not the case, the preserve is declared to be unfit for consumption and the entire batch has to be thrown away.

Under those conditions, and except where a deformation (swelling) of the analysed preserve cans is observed after emission of carbon dioxide due to microbe proliferation, the deterioration in the preserve cans is not detected until the end of the eighth or twenty-second day. This leads to obvious problems of loss and stock management.

In order to overcome that disadvantage, the document FR-A-93 12 829 has already proposed a device permitting continuous control of the contents of preserve cans in order to check the consumable nature thereof by collecting gases in the container or in the can without having to open it.

The prior art device comprises the following elements:

a lid which is identical to those with which the preserve cans of the series to be controlled are equipped and which is to undergo the same operations of crimping onto a can body after the latter has been filled, then autoclaving and preserving, but which is pierced, especially at its median portion, by an opening which is preferably circular, a set of mounting parts screwed to one another on each side of the lid opening in such a manner as to maintain a set of sealing joints and to delimit a control chamber which can be isolated, on the one hand, from the inside of the preserve can and, on the other hand, from the external medium.

the control chamber being subdivided into two cells by a filtering membrane which is permeable to gases but impermeable to micro-organisms and especially to pathogenic germs, namely, on the one hand, a lower cell or receiving cell and, on the other hand, an upper cell or collecting cell, collecting means enabling the impermeability of the control chamber with respect to the inside of the preserve can to be broken in order to allow any gases emitted there to penetrate into the receiving cell, and sealing means enabling the collecting cell to be kept isolated from the external medium, after the lid has been crimped onto the previously filled can body and during the autoclaving and preserving operations.

According to that prior publication, the sealing means comprise a sealing joint which is generally produced from silicone and which is to be pierced by a needle connected to continuous analysis devices in order to permit the collection of gases, especially carbon dioxide, which have penetrated into the control chamber after the impermeability has been broken.

Experience has shown that that configuration is not without disadvantages, bearing in mind that the piercing of the sealing joint often causes the needle to become blocked owing to the penetration of fragments of seal into its internal duct.

In addition, contamination of the filtering membrane has also been observed when the needle has been inserted too deeply.

A first aim of the invention is to overcome those disadvantages by designing a device of which the implementation does not require an operation of cutting into a seal by means of a needle.

To that end, the invention relates to a device of the above-mentioned type which is characterised in that the sealing means comprise a screw capable of co-operating with the set of mounting parts and, where appropriate, with an annular sealing joint, and in that the collecting means comprise a threaded end-part that is to co-operate with the set of mounting parts, replacing the sealing screw and, where appropriate, the annular sealing joint during the control operation, in such a manner as to allow the impermeability of the receiving cell with respect to the container or can to be broken, and that comprises a hole connected to continuous analysis devices in order to enable gases, especially carbon dioxide, which have penetrated into the receiving cell to be collected.

The hole in the collecting end-part may have a substantially greater diameter than has the internal duct of the needle according to the above-mentioned prior art, which improves the reliability of the readings.

The device according to the invention is especially adapted to the control of preserve cans but could of course be used to control and analyse the contents of any closed container, such as, for example, the contents of drums containing chemical products (solvents, paints, . . .), without having to open it.

An important feature of the invention is associated with the fact that the containers or cans controlled may follow the other containers or cans of the same batch all along the production chain and may undergo the same treatments.

It is also important that, owing to the presence of the filtering membrane, the impermeability of the receiving cell with respect to micro-organisms coming from the external medium can be maintained during the analysis process so that any risk of contamination of the internal portion of the container or can which could distort the results obtained is excluded.

By way of example, the continuous analysis devices may be constituted by devices capable of measuring and, where appropriate, representing graphically the variations as a function of time of the conductivity of a solution, especially a potash solution in contact with the collected gases, especially carbon dioxide.

This is a control by impedometry based on the fact that the conductivity of the solution analysed is a function of its concentration of $CO_2$; the principle of a control of this type is known per se.

According to a further feature of the invention, the set of mounting parts comprises two annular parts which are screwed to one another, namely a substantially flat external annular part and an internal annular part comprising a cylindrical portion which is provided, on its external face, with a thread cooperating with a corresponding thread on the external annular part and which is extended by a collar at its lower end.

According to that configuration, the lid is sandwiched, at the level of the periphery of its median opening, between the lower face of the external annular part and the upper face of the collar of the internal annular part.

According to the invention, the upper face of the collar is provided with a peripheral groove receiving a first O-ring seal which is supported against the lower face of the lid in such a manner as to contribute to the impermeability of the control chamber with respect to the internal portion of the container or can and with respect to the external medium.

In order to obtain the device according to the invention, the manufacturer can of course use commercially available lids and provide them with the opening himself; he can then himself, in his factory, position the two annular parts and also the first O-ring seal, which corresponds to the first stages of assembling the device.

According to a further feature of the invention, the internal face of the internal annular part is provided, on the one hand at its upper portion, with a peripheral groove which is to receive a second O-ring seal contributing to the impermeability of the control chamber with respect to the inside of the container or can and with respect to the external medium and, on the other hand at its lower portion, with a thread which is, where appropriate, delimited by a shoulder and which is to cooperate with a corresponding threaded portion of a principal mounting part containing the control chamber.

According to the invention, the principal mounting part is to be screwed onto the internal face of the lid which has previously been equipped with the two annular parts and also with the first and second O-ring seals.

According to a further feature of the invention, the principal mounting part is provided, at its upper portion, with a substantially cylindrical median recess corresponding to the control chamber. The recess comprises a shoulder defining a support surface for the filtering membrane and thus delimiting the receiving cell and the collecting cell.

According to the invention, the principal mounting part is also provided with a peripheral recess having a substantially U-shaped cross-section. The recess comprises a central annular branch and also two side annular branches, namely an external side branch and an internal side branch; he latter branch is pierced at its lower portion with a series of substantially horizontal receiving ducts which open out into the receiving cell, preferably just below the filtering membrane.

The impermeability of the peripheral recess with respect to the external medium and the inside of the container or can is ensured by the two O-ring seals mounted on the internal annular part and also by a third O-ring seal mounted in a peripheral shoulder or groove which is provided for that purpose on the upper face of the external side branch and which is capable of being supported against the lid.

According to a further feature of the invention, the external face of the internal side branch is provided with a thread cooperating with the thread provided on the internal face of the internal annular part in such a manner as to enable the principal mounting part to be secured to the internal annular part after the latter has been mounted on the opening of the lid.

A hexagonal end-part, provided at the lower end of the principal mounting part, enables the latter to be secured more easily to the internal annular part by tightening by means of a spanner.

The internal face of the internal side branch is also provided with a first thread which cooperates with a pierced screw locking the filtering membrane, by means of flat annular seals mounted on each side of the membrane.

According to a basic feature of the invention, the principal mounting part is movable between, on the one hand, a rest position in which the third O-ring seal provided in the external annular branch of the peripheral recess abuts the lid so as to ensure the impermeability of the control chamber with respect to the inside of the container or can, and, on the other hand, a collecting position which is downwardly offset and in which the impermeability is broken and the gases emitted inside the container or can can penetrate into the peripheral recess and then into the receiving cell via the receiving ducts.

Those gases, which are especially carbon dioxide, can then penetrate into the hole in the collecting end-part and pass to the continuous analysis devices.

Tests carried out in a production unit have shown that the average time taken to detect contamination is 48 hours. For security, it is expedient to prolong the test for approximately four days, which nevertheless constitutes a substantial time-saving compared with the devices according to the prior art.

The device according to the invention therefore enables the deterioration in preserve cans belonging to the same batch to be detected very rapidly, so that it is possible to treat the causes of deterioration as soon as possible in the production chain and to limit the number of cans that are unfit for consumption and that have to be destroyed.

The value of the device will therefore be readily appreciated.

According to a further basic feature of the invention, the internal face of the internal side branch is provided, at its upper portion, with a second thread which can cooperate, on the one hand, with the sealing screw and, on the other hand, with the collecting end-part.

The positioning of the end-part makes it possible to achieve, simultaneously, the displacement of the principal mounting part from the rest position to the collecting position and the connection of the control chamber and the continuous analysis devices.

Before breaking the impermeability, and especially during the autoclaving and preserving operations, the various flat seals are squashed by the sealing screw which improves the impermeability of the control chamber with respect to the external medium, it has been demonstrated experimentally that such an assembly can withstand a pressure of up to 1 bar and a partial vacuum of up to 800 mbars.

It should be noted that if the preserve can is always stored in an upright position, it may be knocked over during the manufacturing process, which could give rise to an accumulation, around the external side branch of the peripheral recess, of fats which may congeal in this area and obstruct the passage of the gases emitted when the impermeability of the control chamber with respect to the inside of the container or can is broken; this risk is avoided owing to the mechanical movement corresponding to the breaking of the impermeability which leads to any fats which have accumulated being cracked to free the passage of the emitted gases.

Another "substantial" point of the device according to the invention is associated with the risk that, in the case of a greatly contaminated container or can, liquid may be entrained with the emitted gases when the impermeability is broken and may be propelled by the gas in such a manner that it clogs the filtering membrane.

A further aim of the invention is to eliminate that risk. It should be noted that the horizontal configuration of the receiving ducts and also their positioning just below the level of the filtering membrane are already of a nature to reduce the risk, bearing in mind the presence of two receptacles in which the entrained liquid can collect, one of the receptacles being arranged at the bottom of the receiving cell while the other receptacle, which is annular, is arranged at the bottom of the peripheral recess.

The present invention, however, enables the risk to be almost completely eliminated.

To that end, and according to a further feature of the invention, the device comprises a threaded support end-part which is open at its median portion in the area of which it cooperates with the set of mounting parts in such a manner as to enable the collecting end-part to be positioned, and which is equipped at its periphery with at least two mounting screws positioned to be supported in the area of the crimping of the lid in such a manner as to enable the volume of the container or can to be increased in the region adjacent to the set of mounting parts and especially to the upper portion of the external side branch of the peripheral recess.

That feature permits the artificial creation of a free space or "head space" which eliminates the disadvantage of clogging.

According to a further feature of the invention, the support end-part cooperates with a thread provided for the purpose on the external face of the external annular part.

The support end-part, which enables the lid to be lifted, can be readily positioned by simple screwing after removing the sealing screw, but of course before breaking the impermeability after the collecting end-part has been mounted.

The features of the device for the continuous control of the contents of hermetically sealed containers which forms the subject-matter of the invention will be described in more detail with reference to the appended drawings in which;

DETAILED DESCRIPTION OF THE INVENTION

The description below will be given with consideration to the particular case in which the device is to be used for the continuous control of the stability of preserve cans in order to check the consumable nature thereof. As has been indicated, this example is in no way to be regarded as limiting the invention, and the control device forming the subject-matter of the invention could be used to control continuously the contents of other types of container.

Figure 1:
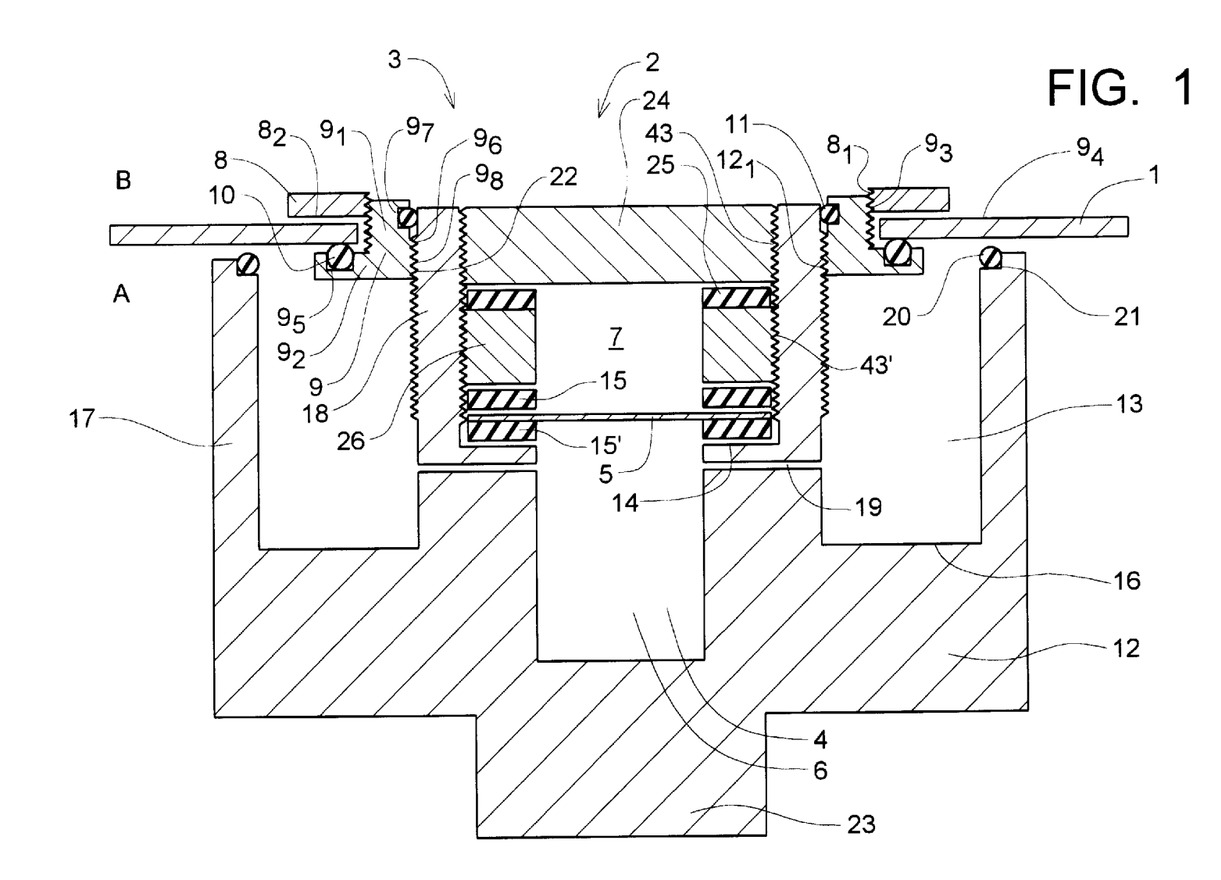
FIG. 1 is a diagrammatic section through the device in a position in which the collecting cell is kept isolated from the external medium by the sealing screw.

According to FIG. 1, the device substantially comprises a lid 1, represented diagrammatically, which is largely identical to those with which the preserve cans of the batch to be controlled are equipped but which is provided at its median portion with a circular opening 2 on each side of which is secured a set 3 of mounting parts, which are screwed to one another, and sealing joints.

The set 3 delimits, at its internal portion, a control chamber 4 which can be isolated, on the one hand, from the inside A of the can and, on the other hand, from the external medium B.

A filtering membrane 5 which is permeable to gases but impermeable to micro-organisms and in particular to pathogenic germs subdivides the control chamber 4 into a lower cell 6 or receiving cell and an upper cell 7 or collecting cell. The respective roles of those two cells 6, 7 will be explained in detail below.

It should be noted that, in the course of this explanation, the adjectives upper and lower refer to the preserve can in the normal upright storage position.

According to FIG. 1, the set of mounting parts 3 comprises a substantially flat external annular part 8 and an internal annular part 9 screwed onto the part 8 on each side of the periphery of the median opening 2 of the lid 1.

To be more precise, the internal annular part 9 comprises a cylindrical portion $9_1$ which is extended at its lower end by a collar $9_2$. The cylindrical portion $9_1$ is provided, on its external face, with a thread $9_3$ which cooperates with a corresponding thread $8_1$ of the external annular part 8. When the two annular parts 8, 9 have when screwed to one another, the lid 1 is in a position in which it is sandwiched, in the area of the periphery of its median opening 2, between the lower face $8_2$ of the external annular part and the upper face $9_4$ of the collar $9_2$ of the internal annular part 9.

The upper face $9_4$ of the collar $9_2$ is provided with a peripheral groove $9_5$ which receives a first O-ring seal 10 which is supported against the lower face of the lid 1.

According to the figures, the internal face $9_6$ of the internal annular part 9 is provided, on the one hand at its upper portion, with a peripheral groove $9_7$ receiving a second O-ring seal 11 and, on the other hand at its lower portion, with a threaded portion $9_8$ which cooperates with a corresponding threaded portion $12_1$ of a principal mounting part or base member l2.

According to FIG. 1, the principal mounting part 12 is provided with a median recess corresponding to the control chamber 4 and also with an annular peripheral recess 13 having a U-shaped cross-section.

The median recess 4 is substantially cylindrical and comprises a shoulder 14 which defines a support surface for the filtering membrane 5 and thus delimits the receiving cell 6 and the collecting cell 7. Two flat annular seals 15, 15' are mounted one on each side of the membrane 5 in order to ensure its positioning and maintenance.

The peripheral recess 13 for its part comprises a central annular branch 16 and also two side annular branches, namely an external side branch 17 and an internal side branch 18; the latter is pierced at its lower portion with a series of substantially horizontal receiving ducts 19 which open out into the receiving cell 6 just below the filtering membrane 5 and the role of which will be described in more detail hereinafter.

It should be noted that the impermeability of the peripheral recess 13 with respect to the external medium B and the inside A of the preserve can is ensured by the two O-ring seals 10 and 11 which are mounted on the internal annular part 9 and also by a third O-ring seal 20 which is mounted in a peripheral shoulder 21 provided on the upper face of the external side branch 17; the third O-ring seal 20 is capable of being supported against the lid 1.

According to FIG. 1, the internal side branch 18 is provided, on its external face, with a thread 22 which cooperates with the thread $9_8$ provided on the internal face $9_8$ of the internal annular part 5, in order to enable the principal mounting port 12 to be mounted on the lid 1 equipped with the two annular parts 8 and 9.

A hexagonal end-part 23 provided at the lower end of the principal mounting part 12 facilitates the mounting operation.

The internal face of the internal side branch 18 is for its part provided with a thread 43 enabling a sealing screw 24 cooperating with a flat annular sealing joint 25 to be positioned in order to keep the collecting cell 7 isolated from the external medium B.

The preserve can equipped with the device according to the invention can therefore undergo the same filling, crimping and autoclaving operations as the preserve cans of the batch to be controlled.

The thread 43 is downwardly extended at the internal portion of the collecting cell 7 by a thread 43' in order to permit the positioning of a pierced screw 26 which squashes and locks the filtering membrane 5.

Figure 2:
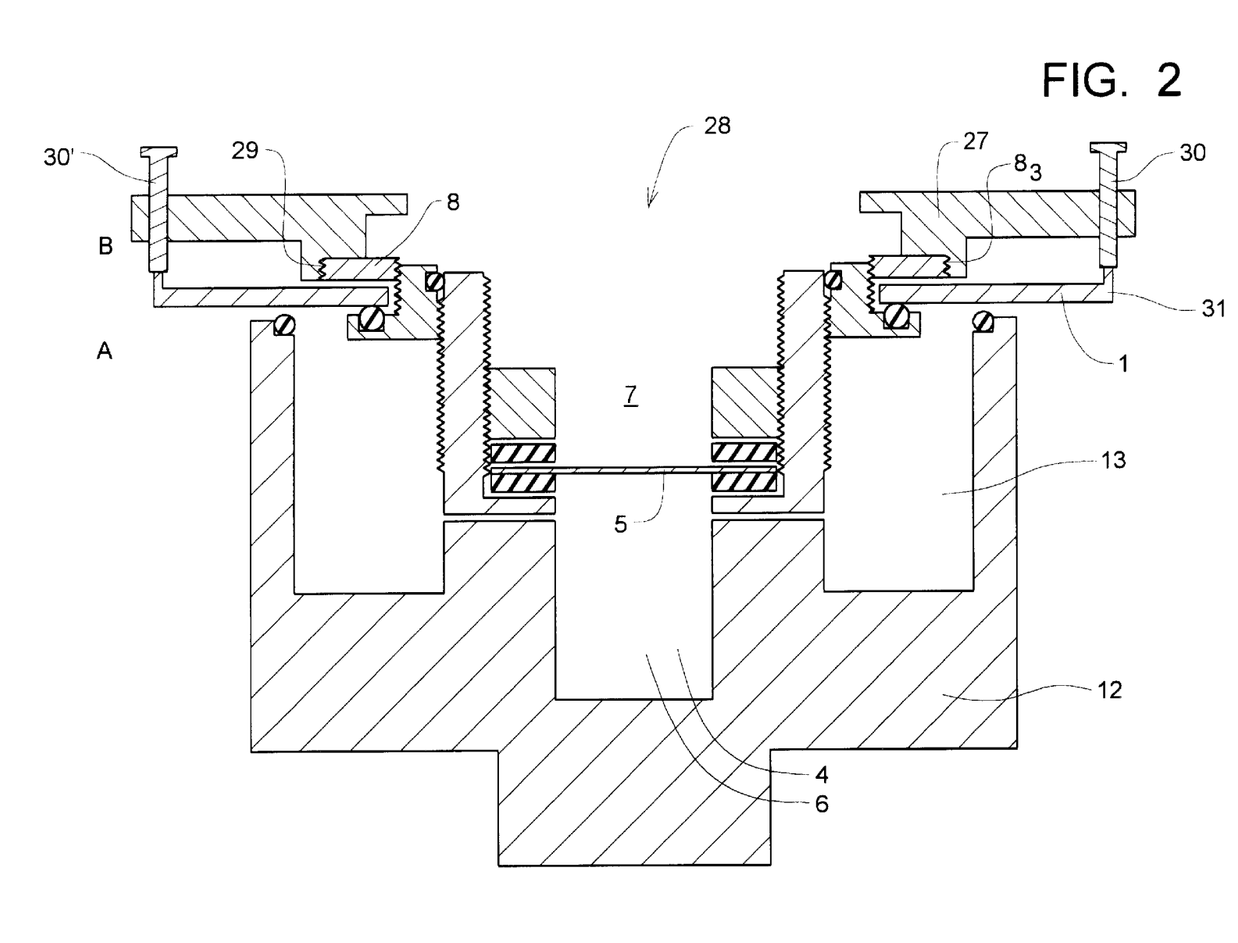
FIG. 2 is a section similar to FIG. 1 but in which the sealing screw has been removed while the support end-part has been put in position.
Figure 3:
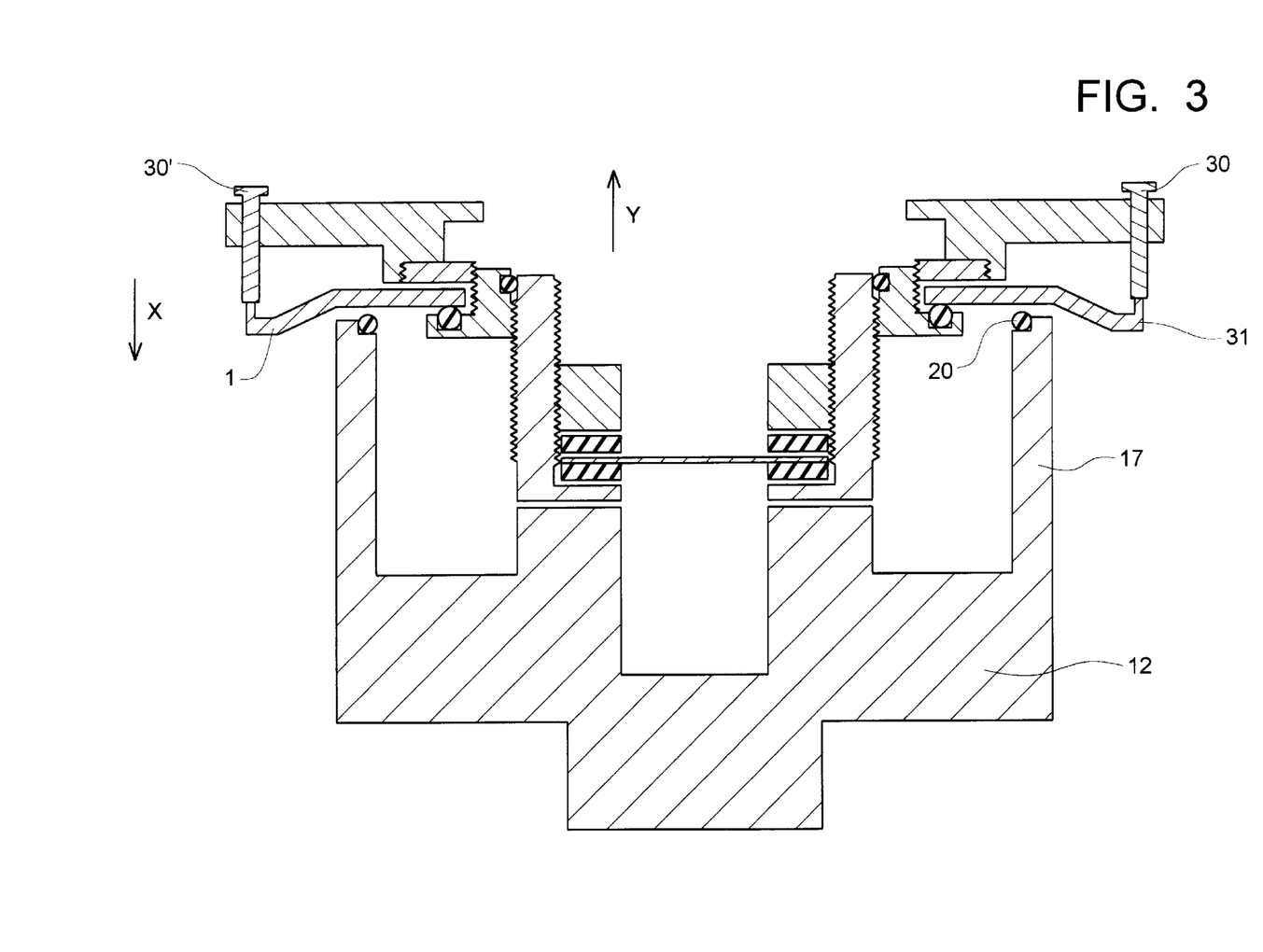
FIG. 3 is a section similar to FIG. 2 but representing the device after the final positioning of the support end-part.
Figure 4:
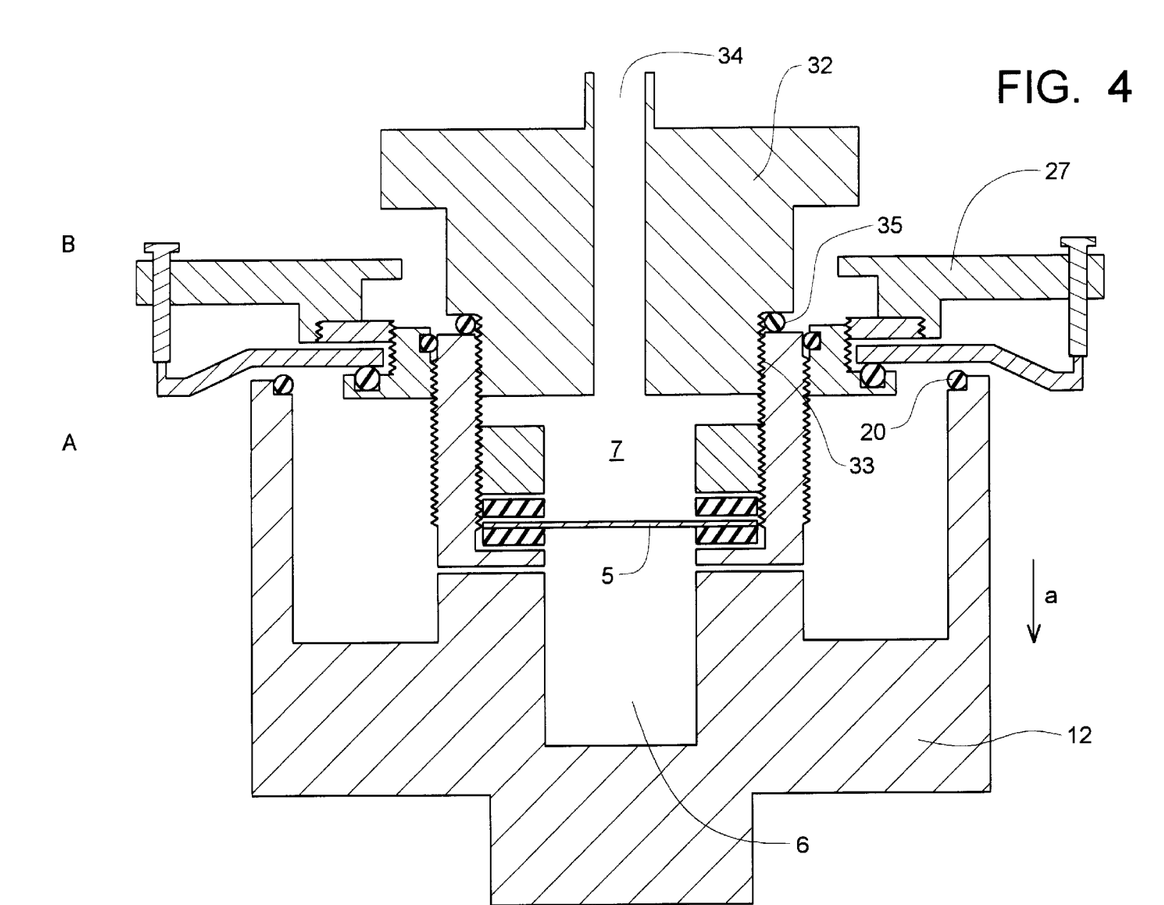
FIG. 4 is a section similar to FIG. 3 but representing the device after the collecting end-part has been mounted.

As shown in FIGS. 2 to 4, during the actual control, the sealing screw 24 and the sealing joint 25 are removed and the collecting cell 7 is brought into contact with the external medium B. The presence of the filtering membrane 5, which may by way of example by a known 0.2 µm filter thus prevents any contamination of the inside A of the can by micro-organisms coming from the external medium B.

To be more precise and according to FIG. 2, the device according to the invention is also equipped with a support end-part 27 which is open at its median portion 28 and which comprises at its internal portion an annular thread 29 which cooperates with a corresponding thread $8_3$ provided on the external face of the internal annular part 8.

The support end-part 27 is provided at its periphery with two mounting screws 30, 30' which are positioned to be supported in the area of the crimping 31 of the lid 1.

According to FIG. 3, the downward displacement of the mounting screws 30, 30' in the direction of arrow X causes the crimping 31 to move down and consequently the central portion of the lid 1 to rise in the direction of arrow Y. Thus, an artificial increase in the volume of the preserve can is obtained in the region adjacent to the principal mounting part 12 and, especially, to the upper portion of the external side branch 17 thereof and of the third O-ring seal 20.

According to FIG. 4, the device is also equipped with a collecting end-part 32 which is introduced into the opening 28 of the support end-part 27 in such a manner as to close the collecting chamber 7 and which comprises a threaded portion 33 cooperating with the thread 43 of the internal face of the internal annular branch 18; the impermeability of the assembly is ensured in this area by an O-ring seal 35 resting on the upper face of the branch 18.

A median through-hole 34 enables the collecting chamber 7 to be connected to continuous analysis devices (not shown).

The threads of the various mounting parts constituting the device according to the invention are designed so that the positioning of the threaded end-part 32 brings about the displacement in the direction of arrow a of the mounting part 12 starting from the rest position shown in the figures towards a collecting position which is downwardly offset and in which the peripheral recess 13 and consequently the control chamber 4 are no longer impermeable with respect to the internal portion A of the preserve can.

In the collecting position, the third O-ring seal 20 is no longer supported against the lower face of the lid 1 and the gases present in the can can penetrate into the peripheral recess 13 and then into the receiving cell 6, passing via the receiving ducts 19; they thus pass into the collecting cell 7 through the filtering membrane 5 and then to the continuous analysis devices.

It should be noted that the artificial increase in the volume of the preserve can, which is obtained owing to the positioning of the support end-part 27, permits maximum avoidance of any entrainment of liquid with the collected gases.

What is claimed is:

1. A method of forming a sealed container from which gasses can be sampled without contaminating contents of the container, the method comprising the steps of:

providing a lid member having an opening formed therein;

providing a base member defining a control chamber;

defining receiving and collecting portions of the control chamber by arranging a filter member within the control chamber, where the filter member is impermeable to pathogens but is permeable to gasses;

providing a first sealing member;

mounting the base member and first sealing member onto the lid member such that the first saling member forms a first seal between the lid member and the base member;

mounting the lid member onto the container such that the first sealing member isolates an interior of the container from the receiving portion of the control chamber;

processing the container to preserve the contents thereof; and moving the base member and the lid member relative to each other to disrupt the first seal between the lid member and the base member and thereby allow gasses within the container to flow into the receiving chamber, through the filter member, and into the collecting chamber for analysis.

2. A method as recited in claim 1, further comprising the steps of:

attaching a second sealing member to the base member before the step of processing the container, where the sealing member prevents fluid flow between the control chamber and an exterior of the container when attached to the base member; and removing the second sealing member from the base member before the step of moving the lid member.

3. A method as recited in claim 1, further comprising the step of:

attaching a sampling member to the base member before the step of moving the lid member; and operatively connecting the sampling member to an analysis device before the step of moving the lid member.

4. A method as recited in claim 2, further comprising the step of:

attaching a sampling member to the base member before the step of moving the lid member; and operatively connecting the sampling member to an analysis device before the step of moving the lid member.

5. A system for analyzing the contents of a hermetically sealed container to check the consumable nature of the contents of the container by collecting gases in the container without allowing micro-organisms into the container, the system comprising:

a can body filled with consumable material;

a lid having a lid opening formed therein, the lid being attached to the can body to form the hermetically sealed container;

a base part attached to the lid to define a control chamber;

a filtering membrane that divides the control chamber into receiving and collecting cells, where the filtering membrane is permeable to gases but impermeable to micro-organisms;

a first seal member for preventing fluid from flowing between the interior of the container and the control chamber when the base part and lid are in a first configuration relative to each other and allowing fluid to flow between the interior of the container and the receiving cell of the control chamber when the base part and the lid are in a second configuration relative to each other; and a moving structure for moving at least one of the base part and the lid relative to at least one of the other of the base part and the lid such that the base part and the lid move between the first and second configurations.

6. A system as recited in claim 5 in which the moving structure further comprises a support member that may be detachably attached to the base member and at least one screw member that threadingly engages the support member, where axial rotation of the screw member displaces the screw member relative to the support member to place the lid in one of the first and second positions.

7. A system as recited in claim 5, further comprising a mounting assembly that engages the lid and the base part such that a seal is formed between the lid and the mounting assembly and between the base part and the mounting assembly.

8. A system as recited in claim 7, in which the mounting assembly comprises first and second mounting parts and second and third seal members, wherein:

the base part is attached to the first mounting part such that the collecting cell of the control chamber is in fluid communication with an external medium surrounding the container;

the second mounting part is attached to the first mounting part such that a mounting portion of the lid surrounding the lid opening is secured between the first and second mounting parts;

the second seal member is secured between the first mounting part and the base part; and the third seal member is secured between the first mounting part and the lid.

9. A system as recited in claim 5, further comprising a mounting assembly comprising:

a first mounting part comprising a first portion that extends through the lid opening and a second portion arranged inside the container; and a second mounting part threaded onto the first portion of the first mounting part outside of the container such that the mounting portion of the lid is arranged between the second portion of the first mounting part and the second mounting part.

10. A system as recited in claim 9, in which the mounting assembly further comprises second and third seal members, wherein:

a first groove is formed on the first portion of the first mounting part, where the first groove is adjacent to the base part;

a second groove is formed on the second portion of the first mounting part, where the second groove is adjacent to the lid;

the second seal member is arranged in the first groove; and the third seal member is arranged in the second groove.

11. A system as recited in claim 8, in which;

the lid opening is circular;

the first and second mounting parts are annular;

inner and outer threaded portions are formed on the first mounting part;

the base part is threaded and engages the inner threaded portion of the first mounting part; and the second mounting part is threaded and engages the outer threaded portion of the first mounting part.

12. A system as recited in claim 5, in which the base part defines a recess in fluid communication with the receiving cell of the control chamber, where the first seal member is arranged to prevent fluid flow from the interior of the container to the recess when the lid is in the first position.

13. A system as recited in claim 12, in which the base part defines a peripheral shoulder that extends around the recess, where the first seal member is supported around the recess and against the lid by the peripheral shoulder when the lid is in the first position.

14. A system as recited in claim 5, in which the base part defines a support shoulder that supports the filtering membrane within the control chamber.

15. A system as recited in claim 14, further comprising a first membrane seal member arranged to prevent fluid flow between the filtering membrane and the support shoulder.

16. A system as recited in claim 12, further comprising receiving ducts extending through the base part to allow fluid communication between the receiving portion of the control chamber and the recess.

17. A system as recited in claim 5, in which;

the base part comprises inner and outer side branches;

the control chamber is defined by the inner side branch;

a support shoulder is formed on the inner side branch within the control chamber, where the support shoulder supports the filtering membrane within the control chamber;

a recess is defined between the inner and outer side branches;

receiving ducts are formed in the inner side branch to allow fluid communication between the recess and the receiving portion of the control chamber;

the first seal member is supported by the outer side branch; and a first membrane seal member is supported by the support shoulder to prevent fluid flow between the filtering membrane and the base part.

18. A system as recited in claim 5, further comprising a sealing assembly that engages the base part to isolate the collecting cell of the control chamber from an external medium surrounding the container during autoclaving of the container to preserve the consumable material.

19. A system as recited in claim 18, in which the sealing assembly comprises a threaded sealing part, where the threaded sealing part engages a threaded portion of the base part to secure the filtering membrane to the base part.

20. A system as recited in claim 19, in which the sealing assembly further comprises first and second membrane seal members, where the first membrane seal member is arranged between the base part and the filtering membrane and the second membrane seal member is arranged between the filtering membrane and the threaded sealing part.

21. A system as recited in claim 5, further comprising a sampling assembly that engages the base part to facilitate the flow of fluid from the collecting cell of the control chamber to an analysis device.

22. A system as recited in claim 21, in which the sampling assembly comprises a threaded sampling part that defines a through hole and engages a threaded portion of the base part such that the fluid flows from the collecting portion of the control chamber to the analysis device through the through hole.

23. A system as recited in claim 21, in which the sampling assembly further comprises a sampling seal member that is arranged to prevent fluid flow between the sampling part and the base part.

24. A system as recited in claim 5, in which the base part comprises a hexagonal portion to facilitate attachment of the base part to the lid.

25. A system as recited in claim 5, in which the base part moves between a rest position and a collecting position, where the base part and the lid are in the first configuration relative to each other when the base part is in the rest position and the base part and the lid are in the second configuration relative to each other when the base part is in the collecting position.

26. A system as recited in claim 5, in which the base part moves between a rest position and a collecting position, where an effective volume of the container is greater when the base part is in the collecting position than when the base part is in the collecting position.

27. A system as recited in claim 21, in which the sampling assembly comprises a sampling part that is threaded onto on the base part, where threading the sampling part onto the base part in a first direction moves the base part from a rest position to a collecting position and in a second direction moves the base part from the collecting position to the rest position, where the base part and the lid are in the first configuration relative to each other when the base part is in the rest position and the base part and the lid are in the second configuration relative to each other when the base part is in the collecting position.

* * * * *